United States Patent [19]
Angelo, Jr.

[11] Patent Number: 5,244,386
[45] Date of Patent: Sep. 14, 1993

[54] DENTAL DIAGNOSTIC DEVICE AND METHOD

[76] Inventor: Patrick J. Angelo, Jr., 722 N. Prospect, Park Ridge, Ill. 60068

[21] Appl. No.: 842,483

[22] Filed: Feb. 27, 1992

[51] Int. Cl.⁵ .............................................. A61C 19/04
[52] U.S. Cl. ...................................... 433/72; 433/140
[58] Field of Search ..................... 433/72, 75, 140; 33/513, 514

[56] References Cited

U.S. PATENT DOCUMENTS

| | | | |
|---|---|---|---|
| 903,344 | 11/1908 | Wackler | 433/140 |
| 3,935,640 | 2/1976 | Cohan | 433/75 |
| 4,364,730 | 12/1982 | Axelsson | 433/72 |
| 5,000,683 | 3/1991 | Brock | 433/75 |
| 5,090,902 | 2/1992 | Lemon et al. | 433/72 |

*Primary Examiner*—John J. Wilson
*Attorney, Agent, or Firm*—Brezina & Ehrlich

[57] ABSTRACT

A gum monitoring device and method is provided for monitoring the dimensions of the crevice between the tooth and the gum. Both preventative monitoring and specific data on existing periodontal disease can now be performed by an individual at home. The device and method will also help in early detection of Periodontal Disease (Gingivitis) which will have a significant benefit for a user's future periodontal condition. The device comprises a gum monitoring instrument having a triangular rigid calibrated shaft with a bullet shaped elongated distal end of predetermined width and length. A handle end on the instrument is a pencil-like, thick handle for easy manual dexterity by the user. The method also includes use of a cheek-lip retractor. The retractor is suggested so that the user may have both better visual access to the area to be monitored, and better physical access of the instrument to the tooth structure to be monitored.

12 Claims, 2 Drawing Sheets

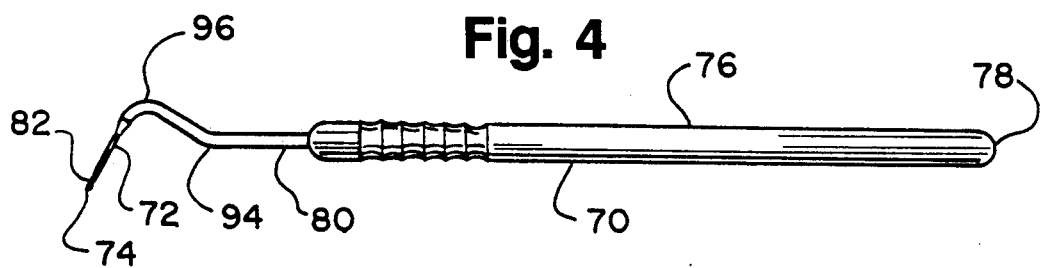
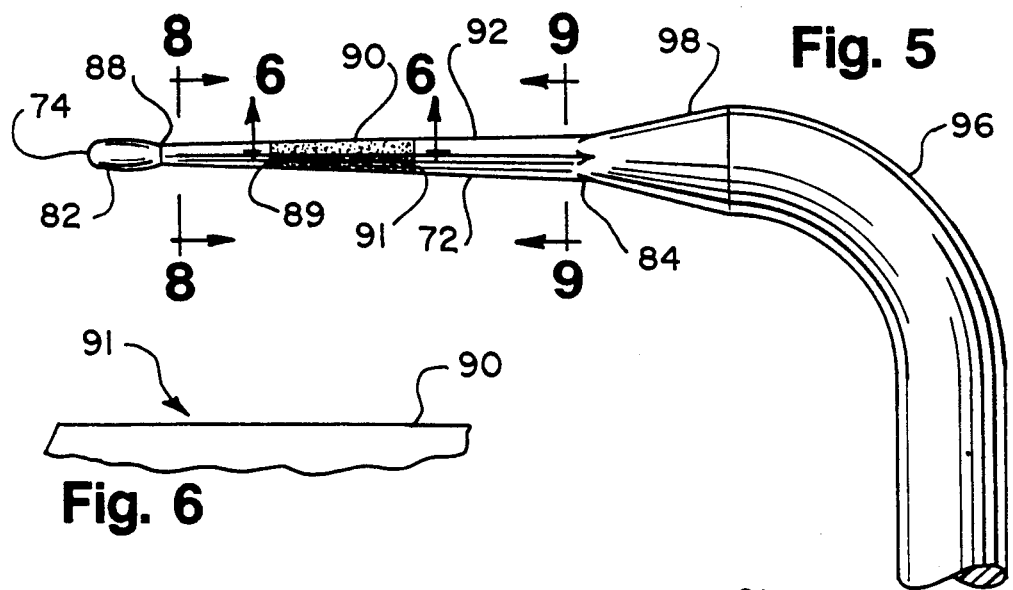
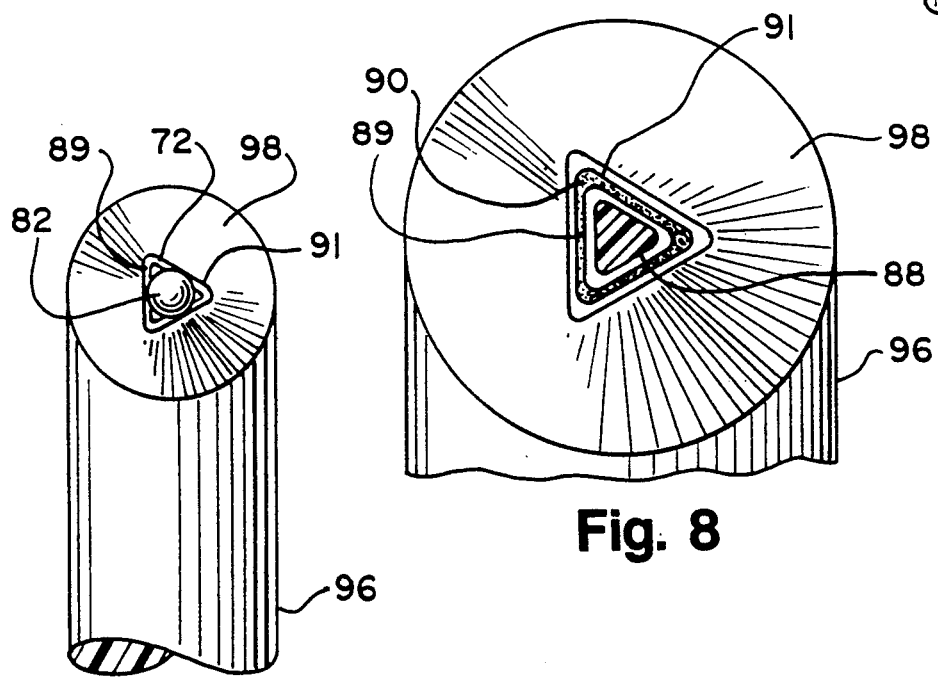
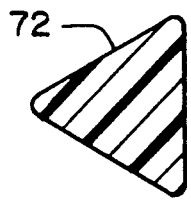

DENTAL DIAGNOSTIC DEVICE AND METHOD

BACKGROUND OF THE INVENTION

An periodontal instrument of plastic has a bullet shaped tip merging into a triangular shaped shaft. This provides greater stiffness and therefore more accurate readings of crevice depths. This shaft is textured between the tip and shaft for better tactile sensitivity. The triangular shape more closely aligns with the front and back surfaces of the teeth (mesial and distal) areas, and the instrument will slide down easier and will read more accurately. Visually contrasting staged or calibrated areas enable observation of health or disease of gum tissue as related to crevice depth and bleeding. This home diagnostic device can then provide data to supplement and assist in dental care suggestions of varying degrees to be determined by a dental team (dentist, dental hygienist).

DESCRIPTION OF RELATED ART

Periodontal disease which effects 70–75 percent of people over 35 years of age. It begins as gingivitis which is an inflammation of the gingiva or gums. If left undetected or not treated, the inflammation will progress to the bone support of the tooth. The destruction of the bone surrounding a tooth will lead to less bone support and thus tooth mobility. If this progression of destruction is continued, tooth loss will eventually occur. However, in most cases, periodontal disease can be maintained and controlled if it is closely monitored and properly treated. The disease can maintain status quo or the condition may be found to have improved with proper dental team care and at home oral hygiene care. Without proper maintenance and monitoring, the condition will most likely deteriorate.

Periodontal disease is caused by dental plaque or bacteria. The deeper a crevice, the more difficult it is for that person or the dental team to remove the bacteria from the depths of these crevices. Thus, periodontal disease tends to advance more rapidly in these crevices.

In the prior art, a metal dental probe is used by the dental profession to detect a periodontal condition at different stages or to determine the periodontal condition of that person. A prior art dental probe when used by a non-professional has a significant potential for harm in penetrating an inflamed crevice, causing an increase in the users discomfort level. Due to discomfort, a home user would also be more tentative (sensitive) in the use of a prior art probe's use and thus not achieve accurate readings. Discomfort will also reduce the home user's confidence in the use of a probe.

SUMMARY OF THE INVENTION

The invention has, as a principal object, the enablement of a person to monitor his or her dental health him or herself. Accordingly, home use in front of a mirror is expected. The reflection of and high visibility of calibrations, configuration and geometry of the instrument, specific arrangement and use of the retractor, interrelation with instructions and packaging as a kit all contribute to this novel invention. Home monitoring is expected to only supplement and assist professional dental care. Definitions of terms of art discussed in this patent application will be familiar to persons of ordinary skill in the art.

One object of the invention is to provide an instrument having an improved, more comfortable tip shape.

Another object of the invention is to provide for placement of a probe in close proximity and in manually controlled relation to a tooth.

Another object is to provide for increased rigidity in the shaft and in the shank of a dental probe to optimize control and accuracy of measurement in use.

Another object of the invention is to provide easily readable calibrations particularly adapted for use at home for self examination.

Another object is to provide for an improved handle with a grip more readily adapted for sure handling by persons at home where the persons have different levels of manual dexterity than dental professionals.

A further object of the invention is to provide a dental instrument having a probe which increases in contact area so as to prevent probing too deeply into furcations.

Another object is to provide improved tactility through the use of a textured calibrated portion abutting the tooth.

In accordance with the invention, the instrument is plastic, such as bright white ABS, with a bullet or ellipsoid shaped distal end or tip so that it will not penetrate the inflamed crevice as easily as prior art configurations. The shaft of the instrument is triangular in shape, the flat surface making it easier to insert the instrument between the tooth and gum and keep the instrument against the tooth surface since the proximal areas being monitored tend to be flat shaped. This triangular shape also allows for less flexibility, the instrument will not bend as easily in a crevice and the user will achieve an accurate reading as to what staged or calibrated area they are reaching. The strength or rigidity factor also allows less chance of the instrument breaking in a deep crevice or furcation area.

The opposite end of the staged or calibrated areas of the instrument comprises a pencil-like thick handle 6 to 7.5mm in diameter, which is analogous to the diameter or width of a common pencil which most of the users have utilized before, but which is significantly greater than the typical calibrated dental probe. The improved handle allows for easier dexterity in the instrument, thus the user will feel more confident in its usage. This improved handle will make it easier for our aging population to use if they lose some dexterity and also acquire arthritis. The thicker handle will also help if someone has a physical limitation, missing fingers, etc. Properly located ridges on the handle provide a guide where to place the fingers, and to provide a better grip to prevent slipping. The instrument handle by comparison to the metal dental probe is easier to use and better accepted for the general public who are not trained in using dental instruments.

In monitoring the gum condition with the instrument, the first calibrated or staged area will be white in color and terminate at a first line 3.5mm from the tip. The second staged or calibrated area will be black in color and 2mm in length from the first line to a second line. The third staged or calibrated area will again be white in color and the length will continue up the shaft of the instrument connecting to the band which leads to the handle. This contrast in colors will enable easier reading of the instrument by the user.

A reading in the first staged or calibrated area is a maintainable crevice. This would be a healthy or normal crevice without any bleeding, a reading of up to 3.5mm. This would suggest the user continue with brushing, flossing and professional periodic cleanings every six months. A reading on the first staged or calibrated area, but bleeding is present, would suggest an early gingivitis. It would be suggested that this person should brush, floss and have plaque or tartar removed from below the gum line by a professional cleaning.

A reading in the second stage or calibrated area is a potential non-maintainable crevice. This area can be up to 5.5mm, bleeding can be present or not. If there is not bleeding, it would be suggested the user brush, floss and again have plaque or tartar removed from below and above the gum line by a professional cleaning. If bleeding is present with a reading in the second staged or calibrated area, the user should brush, floss and seek a comprehensive dental examination, including dental team probing and recording of crevice depths. Also, recent or new full mouth radiographs would be suggested and appropriate therapy will be advised by the dental team. A reading into the third staged or calibrated area is a highly non-maintainable crevice and the user should see a dentist for a comprehensive dental consultation. A complete current set of radiographs would be necessary to determine the proper course of action.

The readings can be taken from the front or mesial aspect of the tooth and the back or distal aspect of the tooth. If the user feels confident in the use of the instrument, he/she may wish to take readings from the lingual (tongue side) or cheek side, depending on individual visualization. Moderate to deep furcation due to increased potential to user's harm are often avoidable because of the increase in thickness of the probe's shaft immediately along and toward the shaft handle in the third stage area. Due to the round tendencies of furcations, the triangular shafts flat surfaces mitigate against probing the round surfaces; a preferable situation, since inaccurate readings or damage to tissue may result from such probing.

The triangular shaft of the instrument will also be textured to allow for greater tactile sensitivity by the user. The user will be more able to feel that the instrument is staying in contact with the side of the tooth. This increase in tactile sensation will also help the user feel the depth of their crevice or to be more aware of the depth of their crevices.

The area between two roots on the mandibular arch and three roots on the maxillary arch on a back tooth are referred to as a furcation. The furcation area is a key area of concern in periodontal disease due to the difficulty in maintenance of oral hygiene in these areas. A furcation area of slight to moderate degree can and must be monitored closely, as rapid destruction of bone can occur in a abscess situation, which furcation areas are prone to experiencing. These areas are susceptible to catching food and/or bacteria and it is harder to keep these areas clean. The instrument should not be inserted past the second staged or calibrated area in a furcation area. If a reading on the instrument is noted in the second staged area or appears to be going into the third staged or calibrated area, the dental team should be seen for a comprehensive examination.

Not all dental office visits include an examination of periodontal crevices. A patient's periodontal condition may not be monitored with impressions, root canal therapy and crown placements, etc. Using the invention in a dental office will allow quick and efficient monitoring of a patient's periodontal condition.

The most widely used metal periodontal probe used today in offices have a number of calibrated markings. The invention has only three simple, clear staged or calibrated areas for the dental team to monitor and chart for the patient and/or user. This will make the periodontal examination easier for the dental team and also more effective. The patient will understand what the dental team is recording because there are only three clearly visible areas to note and it can be explained to the patient with the help of an information or instruction book.

In the preferred embodiment, the device is sold in a kit. The retractor is also a part of the kit. The retractor is a plastic double ended paddle-type device. The retractor is pulled back or out and up or out and down to distend the cheek or lip out of the visual line of view to the instrument and area of the tooth to be monitored. The slight curve up on the larger rounded end is used to hook the corners of the mouth for better retraction and less chance of slipping out from the side of the cheek. This retraction is of importance so the user may be better able to adapt the instrument to the tooth surface to be monitored. The retraction is also necessary to the user so he/she has clear visual access to his/her specific staged or calibrated area on the instrument.

An information or instruction book will also be included in the kit. This information or instruction book will educate the user on not only the stages of periodontal disease, but will also explain exactly what periodontal disease is. An information or instruction book gives specific detailed illustrated directions for the proper technique in the use of the instrument and retractor. An information or instruction book will explain the periodontal condition of the user in relation to a reading in a specific staged or calibrated area. An information or instruction book will also suggest appropriate dental care to be pursued in relation to a reading in a specific staged or calibrated area.

BRIEF DESCRIPTION OF THE DRAWINGS

FIG. 4 is an elevational view of the instrument.

FIG. 5 is an enlarged elevational view showing the tip of the instrument.

FIG. 6 is a sectional view showing a textured surface.

FIG. 7 is an enlarged plane view showing the tip of the instrument.

FIG. 8 is a sectional view of the shaft of the instrument.

FIG. 9 is a sectional view of the shaft of the tip of the instrument.

DETAILED DESCRIPTION OF THE PREFERRED EMBODIMENT

Figure 1:
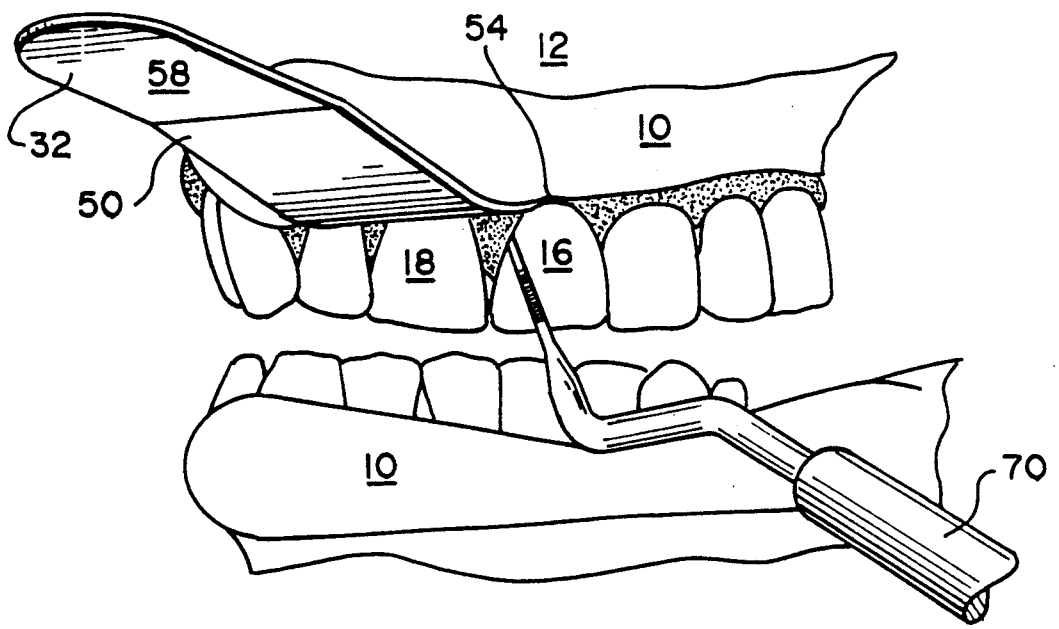
FIG. 1 is an elevational view of the invention in use.
Figure 2:
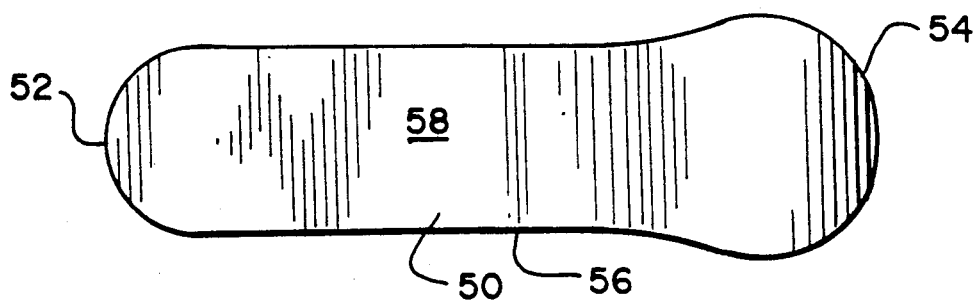
FIG. 2 is a plan view of the retractor.

FIG. 1 shows the kit in use. Retracting lip 10 and cheek 12 is the lip and cheek retractor 50. The retractor is made of ABS bright white plastic which is not harmful for use in the oral cavity. It has sufficient rigidity and section so that it will not deflect unduly when retracting the lips and cheeks which at times are difficult due to strong musculature.

The first end 52 of the retractor is a smaller rounded end approximately 25mm in width. The smaller end is to be held between the thumb and index or middle finger so as to have the control and strength to retract the lip or cheek out of the way so the user may see the staged or calibrated areas on instrument 70 and adapt the instrument to the side of tooth and to reach the instrument to the back teeth.

Figure 3:
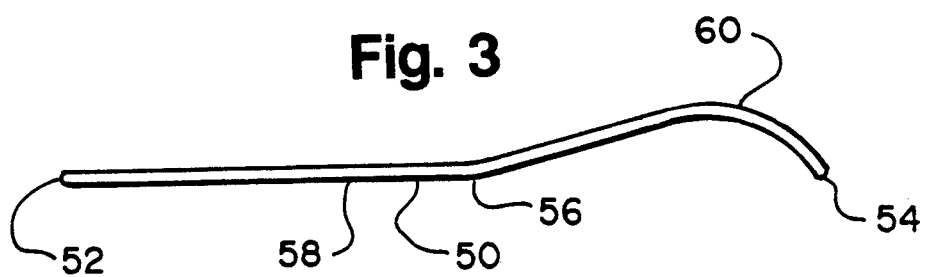
FIG. 3 is an elevational view of the retractor.

Second end 54 of the retractor is approximately 32mm in width. This larger and wider end 54 is placed between the cheek or lip 10,12 and teeth 16,18 and gently pulled up or down to retract the lip or cheek out of the users way. The larger end of the retractor has an approximate 15 degree bend 56 up from the extended line of handle portion 58. Curve 60 (FIG. 3) at end 54 of the retractor allows the user to engage the lip or cheek at the corners of the mouth so the retractor does not slide out from the inner surface of the mouth. The preferred retractor measures approximately 100mm in total length and is a smooth plastic. This smooth surface will not damage the inner cheek surface or the lips. The length of the retractor allows for reaching to the back portions of the mouth for people with deeper posterior areas to monitor. However, those users with a smaller oral cavity may utilize the amount of length needed for acceptable retractor of lip or cheek by shortening up where their fingers hold the retractor. Being that the retractor on the end to be held is smaller and a flat surface, it can be held at different levels on the handle as to make the retractor utilization more comfortable and efficient for each individual.

FIG. 4 illustrates the instrument 70. This instrument is made of a non-toxic ABS bright white plastic for use in the oral cavity. In the preferred embodiment, the instrument 70 is approximately 135mm in length. On one end 74 it has an elongated probe shaft 72 and a pencil-type handle 76 on the other end 78. The handle 76 is approximately 6mm thick throughout. An ordinary metal dental probe handle is only 5.2mm thick tapering down to 3.8mm and it would be more awkward to be used by someone not trained with dental instruments. The approximately 100mm length of handle 76 facilitates the user reaching back teeth and permits shortening up on the handle if necessary for monitoring crevices in the anterior portion of the mouth.

FIG. 4 illustrates seven grooves 77 near the proximal surface of the handle. The purpose for the seven grooves is to further insure a firm grip, especially where surfaces may be moist, and to avoid gripping in other locations. In the preferred embodiment it measures 0.3mm wide by 0.5mm in length.

The tip 82 of the instrument is bullet or ellipsoid in shape. The bullet tip is advantageous in that it is a gentle rather than a sharp point and will be less likely to penetrate an ulcerated crevice and cause damage. The somewhat softer plastic is also less likely to pierce the sulcus lining than a metal probe.

From bullet-shaped tip 82 extending 3.5mm to first line 89 is the initial or first staged or calibrated white area 88. The width with the desired taper from tip 82 to line 89 is about 0.7mm. A reading in this staged or calibrated area would indicate a maintainable crevice without bleeding and slight reversible trouble when bleeding is present (gingivitis).

Contrasting staged or calibrated areas make it easier for the user to visualize and to record an accurate crevice depth. First area 88 extends a total length from the tip 3.5mm to line 89. The second calibrated area 90 is black in color in the preferred embodiment. A great color contrast should exist between staged areas, since home consumers should identify each individual staged area. This area is 2mm in length from line 89 to second line 91. Maintaining taper, the shaft width here is about 0.9mm. This brings the total length from the tip to 5.5mm. A reading in this black area is a potentially nonmaintainable crevice which should be monitored for further changes.

The third staged or calibrated area 92 is white, and continues up the shaft of the instrument connecting to the transition 84 to the shaft 80. At the beginning of transition 84, the width is about 1.3mm. The third calibrated area 92 extends from second line 91 to the transition between the triangular section probe 74 into the round section shaft 80 at conical transition zone 98. Penetration to this area indicate potentially moderate to severe periodontitis.

The instrument has an approximately ninety degree bend 94 following an arc of approximately 25mm in diameter following zone 98. This bend allows the user to line up the instrument adjacent to the side of the tooth so that the instrument is aligned at the proper angle to enter the crevice and facilitate the textured surface of the probe to be generally in contact with the side of the tooth surface as it is inserted to the depth of the crevice, so the instrument will achieve an accurate reading.

An approximately fifteen degree upward bend 94 attaches pencil-like handle 76 and transition 84 to the elongated shaft 80, and thence through normal bend 96 to the probe 74 with the instrument's staged or calibrated areas 88, 90 and 92. These bends enable the user to use the instrument in the mouth around corner areas or hard to reach malpositioned teeth while maintaining firm control through gripping handle 76.

FIGS. 6–9 show in detail the triangular section of the elongated probe 72 adjacent to and supporting the tip 82 of the instrument. In the preferred embodiment its probe may be textured as indicated by the numeral 91 in FIG. 6, enabling the user to have a better tactile sense of feeling when the instrument is placed into the crevice. The triangular shape, when aligned, provides a flat surface of the instrument to more closely contact the side of the tooth than prior art devices because the proximal (or side of the tooth mesial and distal) surfaces of teeth tend to be flat. Thus, if the user can keep the instrument in contact with the tooth and have an improved feel of a crevice depth, the user will achieve more accurate readings and feel more confident in using the instrument. This increase in tactile sensation will also lessen the chance of the user piercing the crevice wall since the user will be more aware of reaching the base of the crevice. The triangular shape of the instrument will also make the instrument more rigid, and thus it will not unduly bend or flex in a deeper crevice. The rigidity factor will also mean that the instrument is less likely to break off in a deeper crevice.

When used, the instrument is placed against the side of a tooth and inserted between the tooth and the gum into the base of the crevice until a slight resistance is felt by the user. The asymmetrical alignment of the triangular section provides for improved ease in handling and insertion in the crevice since a user most often will hold the instrument in one hand thereby permitting lateral angle changes relative to the position of the tooth in the mouth.

This process is performed on the mesial and distal aspects of each tooth to be checked or monitored. The lingual and cheek portion of a tooth may be checked if the user feels confident in the use of the instrument in these areas. The distal end of the instrument or the staged or calibrated areas will be noted by the user so they will be able to determine their periodontal status. The instrument is next removed from one area of a tooth to the next area, or to another tooth of concern, and this process is repeated.

An information or instruction book will discuss and show the user a course of treatment they should seek in relation to their specific staged or calibrated areas they reach within their crevice as illustrated in the instruction booklet. The user of the kit may utilize it as an initial device to determine their generalized periodontal health, or the user may be instructed by his/her dental team to monitor specific areas of concern.

The information or instruction book will explain a reading in the first staged or calibrated area (white) as a crevice with a maximum depth of 3.5mm. This depth may be maintained by the user, and is healthy when no bleeding is present. When bleeding exists in the first staged or calibrated area, then gingivitis is most likely present which with proper treatment is reversible. A reading in the second staged or calibrated area (black) can range from 3.5mm to a maximum 5.5mm. This would alert the user to an area of a deeper crevice and that this area has potential to be non-maintainable by the user. A reading in the third staged or calibrated area (white) is a crevice which is greater than 5.5mm. This most likely is non-maintainable and would suggest that the user monitor this area closely for further change and seek professional dental care immediately.

While designed for home use, the invention may be used in the dental office. A dental team member using the kit in the office will perform a periodontal examination or screening faster and more efficiently. The standard metal dental probe is most often all one color, thus it is sometimes harder to see what probing depths a patient is at. The periodontal exam with the metal dental probe thus would take longer and be more tedious than if they utilized the kit.

As packaged in kit form, the invention in its preferred embodiment will have a sanitary encasement providing advantages in avoidance of confusing members of the same household in using each other's kit, helping in keeping the instrument and retractor more hygienic.

I claim:

1. A periodontal instrument for monitoring and examining the health of gums having a handle at a first end and a probe at a second end, the handle having a first axis and the probe having a second axis oblique to the first axis, comprising:
   a tip at a distal portion of the probe having an ellipsoid shape;
   a shaft coaxial with and supporting the tip;
   said shaft having a plurality of surfaces, a first of said surfaces being a flat surface;
   said tip transitioning smoothly to said shaft surfaces;
   a shank connected to said handle, supporting said shaft and substantially maintaining the angular relationship between the first and second axis.

2. The invention according to claim 1 wherein:
   said shaft further comprises second and third surfaces merging with said first surface to form first, second and third axially extending apexes between said surfaces;
   said first surface being aligned so as to be substantially parallel to the first axis.

3. The invention according to claim 2 wherein:
   said shaft has a section, taken in a plane perpendicular to the second axis, being of a substantially triangular configuration;
   said first, second and third surfaces being flat surfaces flanking said apexes, and being substantially aligned to selectively abut teeth when the probe is in use while providing rigidity to the shaft.

4. The invention according to claim 3 wherein said first, second and third surfaces are textured to provide enhanced tactile sensitivity.

5. The invention according to claim 3 wherein:
   said shank has a conical zone providing a surface transition to said shaft, said shank being substantially circular in section.

6. The invention according to claim 5, wherein said shaft has a first bend near the handle and a second, substantially normal bend intermediate the first bend and the conical zone;
   said bends providing increased reach into the mouth of a user and maintaining the angular relation between the first and second axes.

7. The invention according to claim 1 wherein:
   said shaft is tapered and gradually increases in cross-sectional area in a direction away from said tip to avoid damage to deeper areas of the gums when inserting said instrument into a deep crevice by preventing said instrument from being inserted too deeply into said crevice.

8. A self-conducted dental diagnostic method for performance by a person observing an open mouth defined by cheeks and lips, and having teeth and gum tissue, with a mirror, comprising the steps of:
   retracting said cheeks and lips with a retractor;
   locating a tooth-gum intersection which defines a gum crevice having a top and a bottom;
   inserting an instrument having a tapered shaft with a tip end and three flat faces in a triangular cross-section configuration into said crevice, one of said flat faces being aligned adjacent said tooth and said tip being inserted to the bottom of said crevice;
   the step of aligning said instrument including maintaining one of said flat faces in contact with said tooth by adjusting the lateral angle of a handle of the instrument to the tooth depending on the location of the tooth in the mouth and in which hand the person is holding the instrument;
   reading the depth of said crevice by comparing the top of said crevice to said inserted shaft, said shaft being calibrated at a plurality of intervals spaced from said tip end;
   determining a course of remedial action by comparing the depth of the crevice to standards provided in instruction material;
   repeating the steps until each tooth-gum intersection has been monitored.

9. The method according to claim 8, wherein the step of retracting said cheeks and lips is accomplished by engaging a curved end of said retractor with said lips and applying pressure generally upwardly on an upper lip or generally downwardly on a lower lip.

10. The method according to claim 8, wherein the step of reading said depth includes observing the color of the inserted shaft at the place where the top is adjacent the shaft.

11. The method according to claim 10, wherein the step of reading said depth includes determining said color to be one of a first color tip-ward of said first interval, and a second color contrasting to said first color and being between said plurality of intervals.

12. The method for determining the condition of human gums by inserting a calibrated textured instrument in a crevice having a bottom and a top edge and being defined by a tooth and gum comprising:

positioning a substantially flat side of a tapered calibrated probe shaft against said tooth, said shaft terminating in an ellipsoidal tip;

said shaft being calibrated at a first line and a second line;

said shaft tapering at a constant angle to said second line from the tip;

inserting said shaft into said crevice;

contacting said ellipsoidal tip of said instrument with, but not piercing said bottom of said crevice;

reading the position of said top relative to said first and second lines;

observing whether or not bleeding of the gum occurs;

determining a course of treatment corresponding to further routine monitoring when the top of the gum is at or closer to the tip than the first line and bleeding is absent;

treating for gingivitis when the top of the gum is at closer to the tip than the first line and bleeding is present;

treating for gingivitis and monitoring for further changes if the top of the gum is between the first and second lines; and treating for potentially moderate to severe periodontics if the top of the gum is at or further from the tip than the second line.

* * * * *